(12) United States Patent
Hochschuler et al.

(10) Patent No.: US 8,157,865 B2
(45) Date of Patent: Apr. 17, 2012

(54) APPARATUS AND METHOD FOR STABILIZING ADJACENT BONE PORTIONS

(76) Inventors: Stephen Hochschuler, Paradise Valley, AZ (US); Matthew N. Songer, Marquette, MI (US)

( * ) Notice: Subject to any disclaimer, the term of this patent is extended or adjusted under 35 U.S.C. 154(b) by 71 days.

(21) Appl. No.: 12/692,503

(22) Filed: Jan. 22, 2010

(65) Prior Publication Data

US 2010/0185292 A1 Jul. 22, 2010

Related U.S. Application Data

(60) Provisional application No. 61/146,616, filed on Jan. 22, 2009.

(51) Int. Cl.
*A61F 2/44* (2006.01)

(52) U.S. Cl. ..................... 623/17.16; 606/279

(58) Field of Classification Search ............... 606/246, 606/248, 249, 279, 90; 623/17.11–17.16
See application file for complete search history.

(56) References Cited

U.S. PATENT DOCUMENTS

| | | |
|---|---|---|
| 515,168 A | 2/1894 | Rasner |
| 4,257,129 A | 3/1981 | Volz |
| 4,349,921 A | 9/1982 | Kuntz |
| 4,479,491 A | 10/1984 | Martin |
| 4,599,086 A | 7/1986 | Doty |
| 4,714,469 A | 12/1987 | Kenna |
| 4,759,766 A | 7/1988 | Buettner-Janz et al. |
| 4,863,476 A | 9/1989 | Shepperd |
| 4,863,477 A | 9/1989 | Monson |
| 4,904,261 A | 2/1990 | Dove et al. |
| 4,917,704 A | 4/1990 | Frey et al. |
| 4,932,975 A | 6/1990 | Main et al. |
| 4,946,378 A | 8/1990 | Hirayama et al. |
| 4,955,908 A | 9/1990 | Frey et al. |
| 5,011,484 A | 4/1991 | Bréard |
| 5,015,247 A | 5/1991 | Michelson |
| 5,108,438 A | 4/1992 | Stone |
| 5,123,926 A | 6/1992 | Pisharodi |
| 5,171,281 A | 12/1992 | Parsons et al. |
| 5,192,327 A | 3/1993 | Brantigan |
| 5,258,043 A | 11/1993 | Stone |
| 5,306,307 A | 4/1994 | Senter et al. |
| 5,306,309 A | 4/1994 | Wagner et al. |
| 5,320,644 A | 6/1994 | Baumgartner |
| 5,360,430 A | 11/1994 | Lin |
| 5,397,364 A | 3/1995 | Kozak et al. |
| 5,401,269 A | 3/1995 | Büttner-Janz et al. |
| 5,425,772 A | 6/1995 | Brantigan |

(Continued)

OTHER PUBLICATIONS

International Search Report, dated Sep. 17, 2010, for International Application No. PCT/US2010/045157.

*Primary Examiner* — Eduardo C Robert
*Assistant Examiner* — Christiana Negrelli
(74) *Attorney, Agent, or Firm* — Wood, Phillips, Katz, Clark & Mortimer

(57) ABSTRACT

An apparatus and method for stabilizing first and second adjacent bone portions. The apparatus has a spacer configured to be placed between the first and second bone portions and at least one stabilizer configured to be joined: a) to each of the first bone portion and the spacer; and b) to at least one of the first bone portion and spacer by being translated relative to the at least one of the first bone portion and spacer.

25 Claims, 11 Drawing Sheets

U.S. PATENT DOCUMENTS

| | | |
|---|---|---|
| 5,425,773 A | 6/1995 | Boyd et al. |
| 5,484,437 A | 1/1996 | Michelson |
| 5,514,180 A | 5/1996 | Heggeness et al. |
| 5,522,899 A | 6/1996 | Michelson |
| 5,534,028 A | 7/1996 | Bao et al. |
| 5,549,679 A | 8/1996 | Kuslich |
| 5,562,736 A | 10/1996 | Ray et al. |
| 5,562,737 A | 10/1996 | Graf |
| 5,562,738 A | 10/1996 | Boyd et al. |
| 5,569,246 A | 10/1996 | Ojima et al. |
| 5,571,189 A | 11/1996 | Kuslich |
| 5,593,409 A | 1/1997 | Michelson |
| 5,609,634 A | 3/1997 | Voydeville |
| 5,609,635 A | 3/1997 | Michelson |
| 5,658,335 A | 8/1997 | Allen |
| 5,716,415 A | 2/1998 | Steffee |
| 5,749,916 A | 5/1998 | Richelsoph |
| 5,888,223 A | 3/1999 | Bray, Jr. |
| 6,241,769 B1 | 6/2001 | Nicholson et al. |
| 6,743,257 B2 | 6/2004 | Castro |
| 7,147,665 B1 | 12/2006 | Bryan et al. |
| 7,255,698 B2 | 8/2007 | Michelson |
| 7,594,931 B2 | 9/2009 | Louis et al. |
| 2004/0193271 A1* | 9/2004 | Fraser et al. ............... 623/17.11 |
| 2005/0149193 A1* | 7/2005 | Zucherman et al. ....... 623/17.11 |
| 2005/0256582 A1 | 11/2005 | Ferree |
| 2006/0074421 A1 | 4/2006 | Bickley et al. |
| 2006/0235535 A1 | 10/2006 | Ferree et al. |
| 2006/0276897 A1 | 12/2006 | Winslow et al. |
| 2008/0208345 A1 | 8/2008 | Hurlbert et al. |
| 2009/0254127 A1 | 10/2009 | Pazanowski et al. |
| 2010/0204737 A1 | 8/2010 | Bae et al. |
| 2010/0204739 A1 | 8/2010 | Bae et al. |
| 2010/0204796 A1 | 8/2010 | Bae et al. |

* cited by examiner

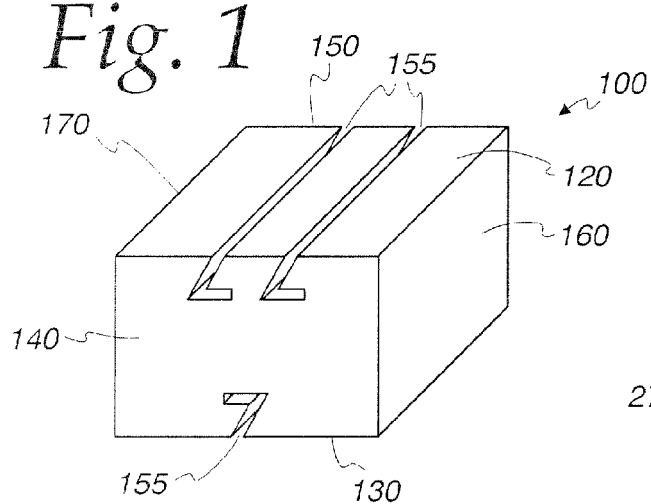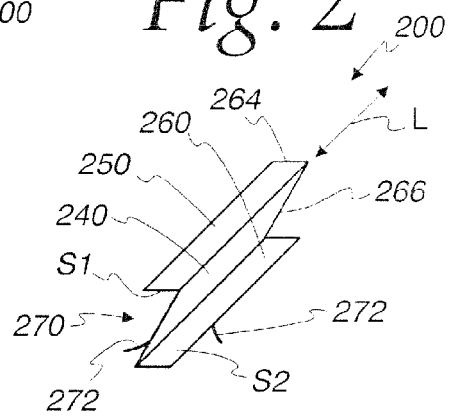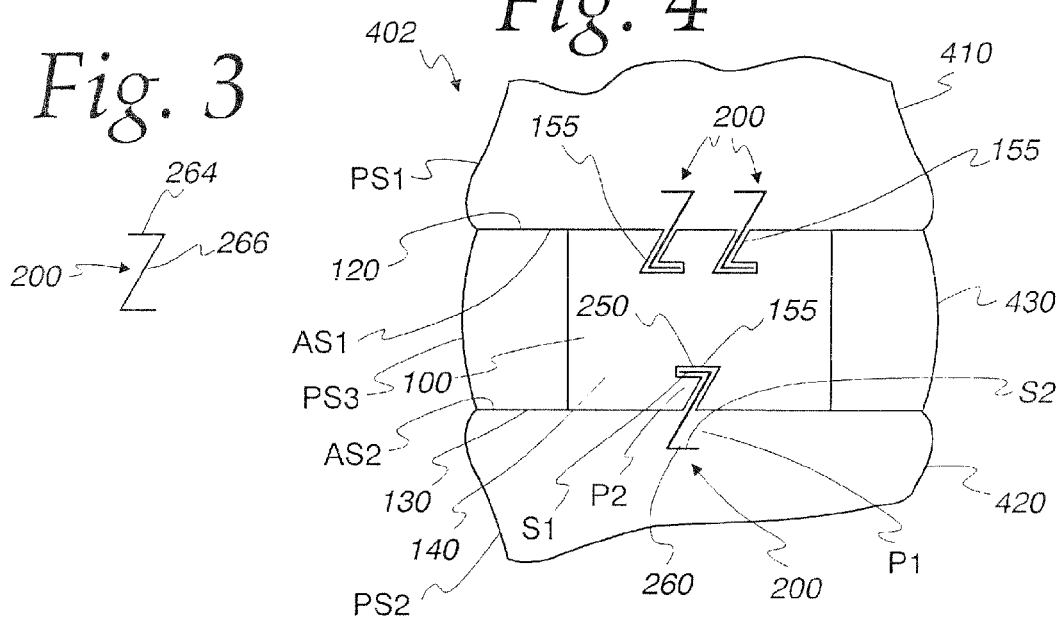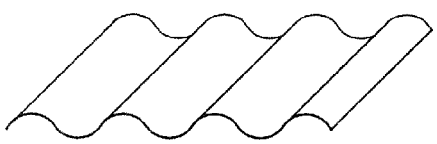

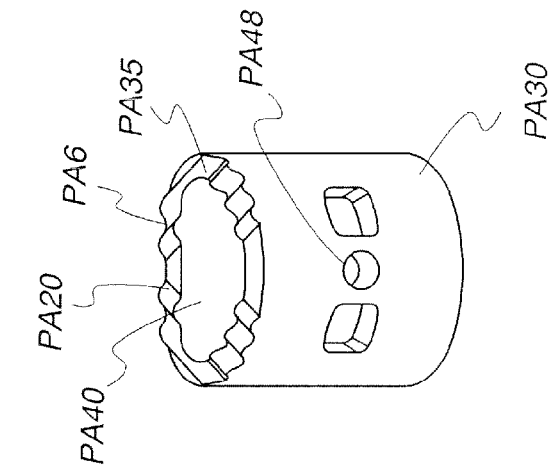
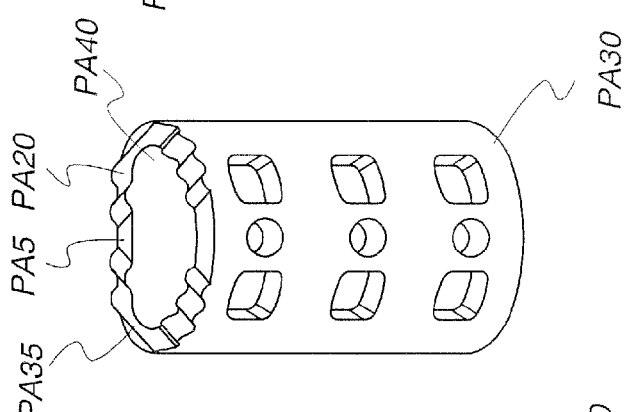
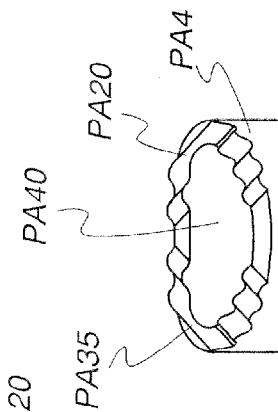
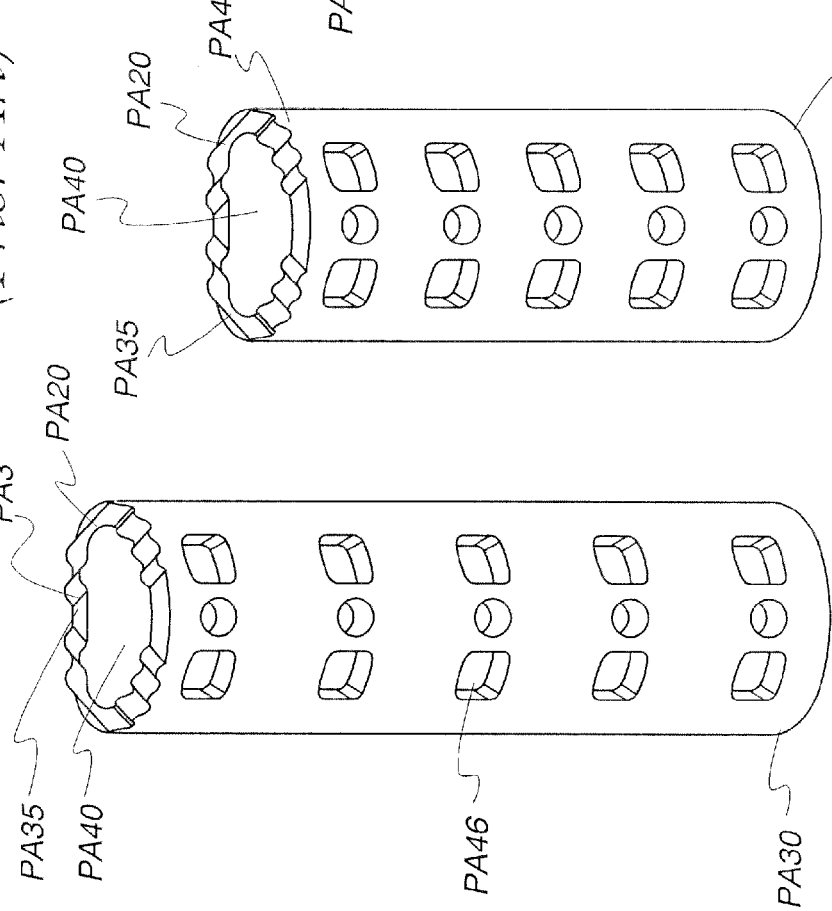
Fig. 8C (Prior Art)
Fig. 8D (Prior Art)
Fig. 8E (Prior Art)
Fig. 8F (Prior Art)

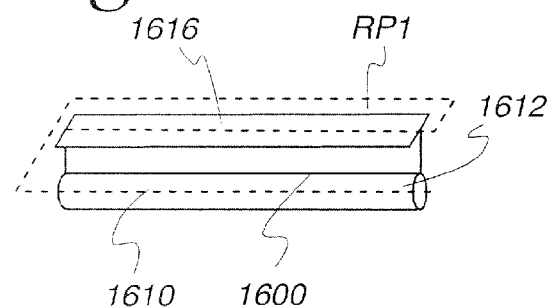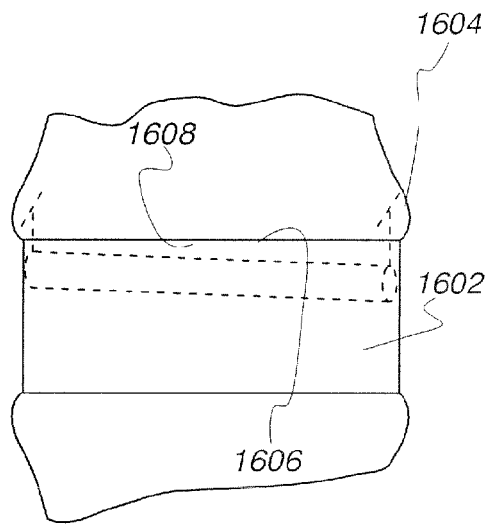
Fig. 16
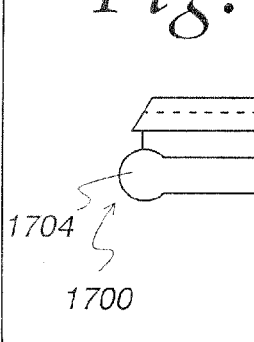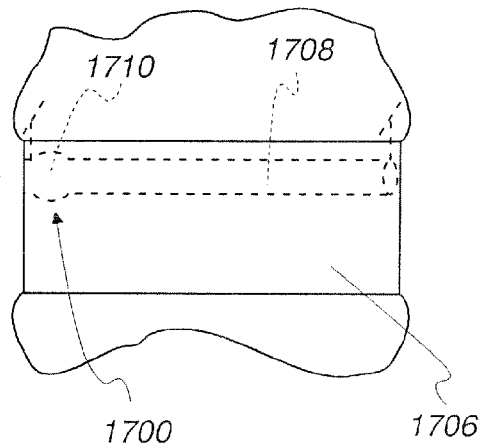
Fig. 17
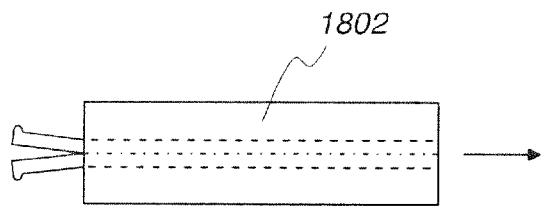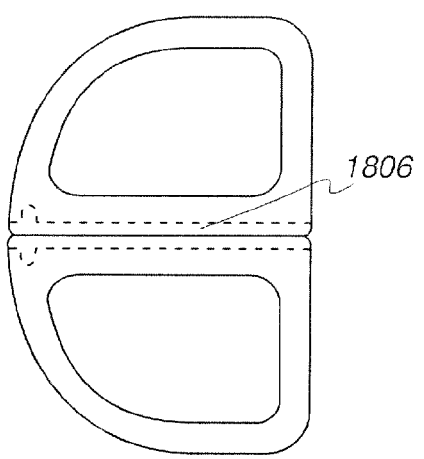
Fig. 18

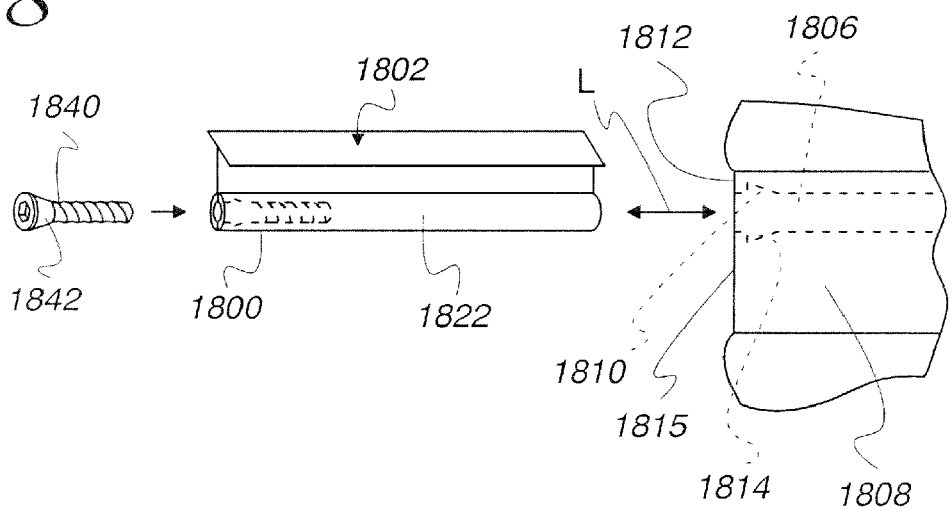
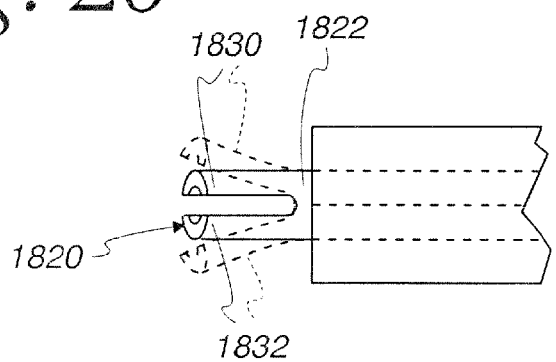
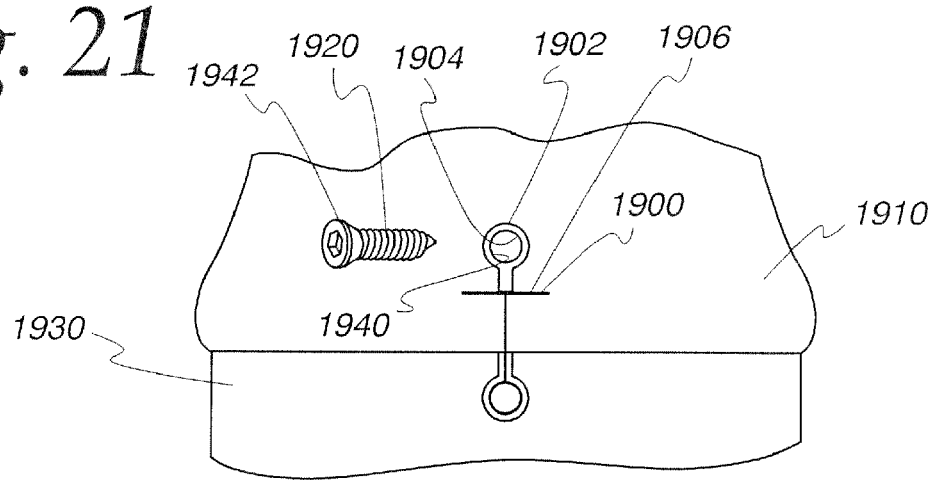

APPARATUS AND METHOD FOR STABILIZING ADJACENT BONE PORTIONS

BACKGROUND OF THE INVENTION

1. Field of the Invention

The present invention relates generally to the stabilization of adjacent bone portions, and more particularly to an apparatus for securing interbody spacers between the adjacent bone portions. The invention is also directed to a method for stabilizing the adjacent bone portions.

2. Background Art

Many different medical procedures are performed that require the stabilization of adjacent bone portions through the securing of an interbody spacer to the adjacent bone portions. Examples of these spacers are those known in the field as interbody cages, corpectomy cages, osteotomy wedges, joint spacers, bone void fillers, etc.

As one example, spacers are used to fuse joints. Spacers are also used to repair complex fractures where bone is missing and in bone regions where there are otherwise voids, as when a tumor and adjacent bone are removed. Spacers are also used in the performance of osteotomies by placing the spacers between adjacent bone portions to perform a wedging action, as to straighten a bone. This list is not exhaustive of the medical procedures that require the placement of a spacer between adjacent bone portions.

In each procedure, the spacer placed between the bone portions is required to be rigidly joined to the adjacent bone portions. A multitude of different apparatus have been devised for this purpose, with many requiring the insertion of screws. While screws are generally effective for this purpose, they are limited in the sense that they do not afford stability in all dimensions required to effect the optimal or desired rigidity.

Spacers are commonly used in spinal repair and reconstruction. The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibro-cartilaginous bodies.

The intervertebral fibro-cartilages are also known as intervertebral disks and are made of a fibrous ring filled with pulpy material. The disks function as spinal shock absorbers and also cooperate with synovial joints to facilitate movement and maintain flexibility of the spine. When one or more disks degenerate through accident or disease, nerves passing near the affected area may be compressed and are consequently irritated. The result may be chronic and/or debilitating back pain. Various methods and apparatus have been designed to relieve such back pain, including spinal fusion using a suitable graft or interbody spacer using techniques such as Anterior Lumbar Interbody Fusion (ALIF), Posterior Lumbar Interbody Fusion (PLIF), or Transforaminal Lumbar Interbody Fusion (TLIF) surgical techniques. The implants used in these techniques, also commonly referred to as vertebral body replacement (VBR) devices, are placed in the interdiscal space between adjacent vertebrae of the spine.

Ideally, a fusion graft should stabilize the intervertebral space and become fused to adjacent vertebrae. Moreover, during the time it takes for fusion to occur, the graft should have sufficient structural integrity to withstand the stress of maintaining the space without substantially degrading or deforming and have sufficient stability to remain securely in place prior to actual bone ingrowth fusion.

One significant challenge to providing fusion graft stability (prior to actual bone ingrowth fusion) is preventing spinal extension during patient movement.

Distraction of the vertebral space containing the fusion graft may cause the graft to shift or move, disrupting bone ingrowth fusion and causing pain.

Generally, existing spinal fusion technology has been limited or lacking in certain respects. Among the limitations of certain of these systems is the requirement that complicated steps be performed to effect their use. Others of these systems lack the optimal multi-dimensional stability, while others are less than desirable because they utilize components that project to externally of one or more of the bone portions between which the spacer is located.

The systems that rely upon the use of screws normally have such limitations. Generally these systems do not effectively allow compression forces to be generated between the spacers and adjacent bone portions. Further, while the screws stabilize the bone-spacer junction in one plane, that is normally flexion-extension, they do not control bending in planes orthogonal to the plane of the screw, that is normally side-to-side bending.

A further problem with existing systems is that parts typically are not locked and are thus prone to working loose. Screws, for example, may loosen over time in the absence of incorporating some structure that effectively prevents turning or lengthwise movement that results in partial or full separation from the bone portions and/or spacers that they penetrate.

The medical field is constantly seeking system designs that might be efficiently and consistently installed and that, most significantly, will effect the desired fusion in a manner that will be safe and reliable for the patient.

SUMMARY OF THE INVENTION

In one form, the invention is directed to an apparatus for stabilizing first and second adjacent bone portions. The apparatus has a spacer configured to be placed between the first and second bone portions and at least one stabilizer configured to be joined: a) to each of the first bone portion and the spacer; and b) to at least one of the first bone portion and spacer by being translated relative to the at least one of the first bone portion and spacer.

In one form, the apparatus is used in combination with first and second bone portions between which the spacer is placed and wherein the at least one stabilizer is joined to each of the first bone portion and spacer.

In one form, the stabilizer has first and second walls with facing surfaces and a part of the first bone portion and the spacer are captive between the facing surfaces on the stabilizer to stabilize the first bone portion and spacer.

In one form, the spacer has a pre-formed channel to receive the at least one spacer.

In one form, the stabilizer is joined to the first bone portion by being translated relative to the first bone portion along a first line. The first bone portion has a first dimension extending along the first line and the first wall extends into the first bone portion over a majority of the first dimension.

In one form, at least one of the facing surfaces has a substantial dimension transverse to the first line.

In one form, each of the facing surfaces has a substantial dimension transverse to the first line.

In one form, the spacer has a second dimension extending along the first line and the second wall extends into the spacer over a majority of the second dimension.

In one form, the stabilizer is configured to be joined: a) to each of the second bone portion and spacer; and b) to at least one of the second bone portion and spacer by being translated relative to the at least one of the second bone portion and spacer.

In one form, the first bone joint member and spacer have adjacent facing surfaces and the stabilizer extends through one of the adjacent facing surfaces.

In one form, the stabilizer extends continuously through each of the adjacent facing surfaces.

In one form, the facing surfaces are configured so that the first bone portion and spacer are progressively urged against each other as the stabilizer is translated relative to the first bone portion and spacer.

In one form, the stabilizer is translatable relative to the first bone portion into an operative position and there is a locking assembly on the stabilizer that maintains the stabilizer in the operative position with the spacer between the first and second bone portions.

In one form, the locking assembly includes cooperating snap fit connecting parts, one each on the spacer and at least one stabilizer.

In one form, the locking assembly is reconfigurable between an assembly state and a locked state.

In one form, the locking assembly includes a reconfigurable wall and a spreader element that is directed into the reconfigurable wall to change the locking assembly from the assembly state into the locked state.

In one form, the locking assembly has a locking tab on the at least one stabilizer that overlies at least one of the first bone portion and spacer and is secured to the at least one of the first bone portion and spacer.

In one form, the first wall has openings therein into which the bone in the first bone portion can grow to thereby secure the first wall to the first bone portion.

In one form, the first and second bone portions are adjacent vertebrae.

In one form, the spacer has oppositely facing surfaces each facing one of the first and second bone portions. The stabilizer is joined to the first bone portion by being translated relative to the first bone portion along a first line that is substantially parallel to at least one of the oppositely facing spacer surfaces.

In one form, the first bone portion and spacer each has an exposed peripheral surface and the stabilizer does not project from either of the exposed peripheral surfaces.

In one form, the spacer has oppositely facing surfaces each facing one of the first and second bone portions and the stabilizer extends only partially through the spacer between the oppositely facing spacer surfaces.

The invention is further directed to a method for stabilizing first and second adjacent bone portions. The method includes the steps of: providing a spacer; placing the spacer between the first and second adjacent bone portions; providing a stabilizer; joining the stabilizer to the spacer; and joining the stabilizer to the first bone portion by translating the stabilizer relative to the first bone portion along a first line.

In one form, the spacer has first and second oppositely facing surfaces each facing one of the first and second bone portions. The step of translating the stabilizer involves translating the stabilizer relative to the first bone portion along a first line that is substantially parallel to at least one of the oppositely facing surfaces.

In one form, the first bone portion has a surface that faces the first surface on the spacer and the step of translating the stabilizer involves translating the stabilizer so that the stabilizer extends through each of the surface on the first bone portion and the first spacer surface.

BRIEF DESCRIPTION OF THE DRAWINGS

FIG. 1 is a schematic, perspective view of one embodiment of an interbody spacer showing a superior surface and an anterior surface thereof;

FIG. 2 is a perspective view of one embodiment of a stabilizer;

FIG. 3 is an end view of the stabilizer of FIG. 2;

FIG. 4 is an end plan view of the spacer of FIG. 1 inserted between two vertebrae with the stabilizers of FIG. 2 anchoring the spacer to the vertebrae;

FIG. 5A is a top perspective view of another embodiment of a stabilizer;

FIG. 5B is an end view of the stabilizer of FIG. 5A;

FIGS. 8A-M depict various conventional embodiments of interbody spacers;

FIG. 16 is a view as in FIG. 15 wherein a different configuration of stabilizer and spacer are used to perform as described for the corresponding components in FIG. 16;

FIG. 17 is a view as in FIGS. 15 and 16 showing a further modified form of stabilizer with one form of locking assembly to maintain the stabilizer in place;

FIG. 18 is an enlarged, plan view of a modified form of locking assembly on a stabilizer and spacer and with locking assembly components on the stabilizer configured as they would be with the locking assembly in a locked state;

FIG. 19 is a perspective view of a modified form of stabilizer and spacer, similar to that shown in FIG. 18, with a locking assembly thereon in an assembly state, the stabilizer aligned to be directed into the spacer and abutted bone portion and with a spreader element aligned to be directed into the stabilizer to change the locking assembly from the assembly state into a locked state;

FIG. 20 is an enlarged, fragmentary, plan view of the stabilizer in FIG. 19 with the locking assembly component on the stabilizer shown in solid lines as it is configured with the locking assembly in an assembly state and in dotted lines as it is configured with the locking assembly in the locked state; and FIG. 21 is an elevation view of a modified form of stabilizer joined with a spacer and bone portion with a locking tab secured against the bone portion with a fastener.

DETAILED DESCRIPTION OF THE PREFERRED EMBODIMENT

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

FIG. 1 illustrates schematically one embodiment of an interbody spacer 100. The spacer 100 can be used between any adjacent bone portions, such as members at a joint, in a void between such joint portions as might be developed by a fracture, through a procedure that removes bone as with a tumor, etc. While the invention is contemplated for use with virtually any adjacent bone portions between which a spacer is required, the initial disclosure herein will be directed towards spinal procedures wherein the spacer 100 is placed between adjacent vertebrae/joint members that make up a subset of the more generically referenced bone portions.

Figure 8A:
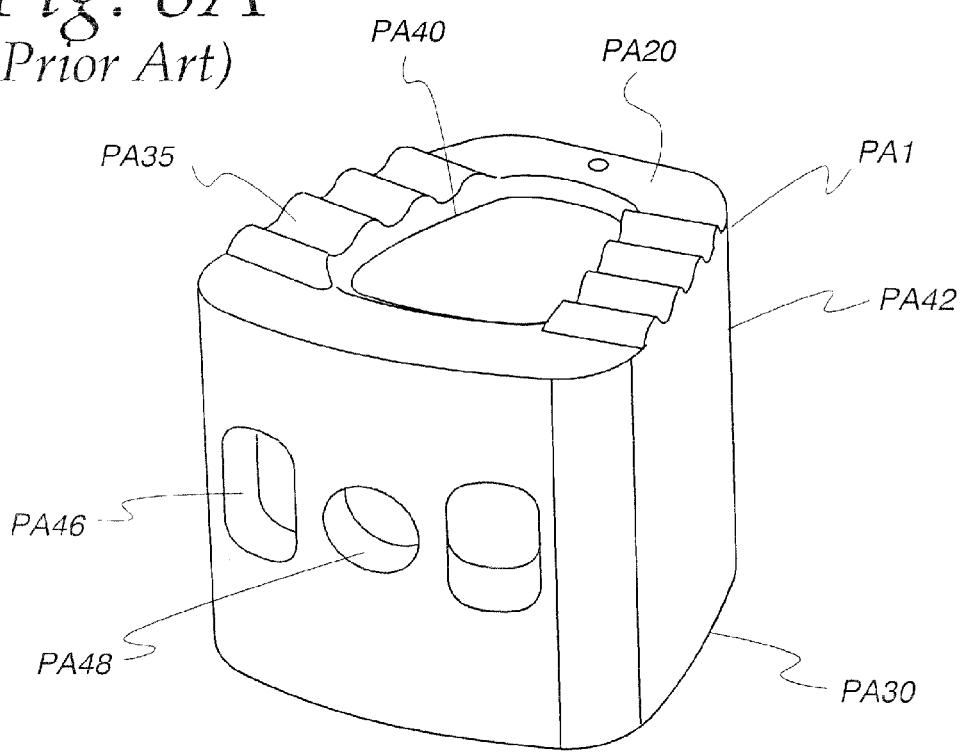
Figure 8B:
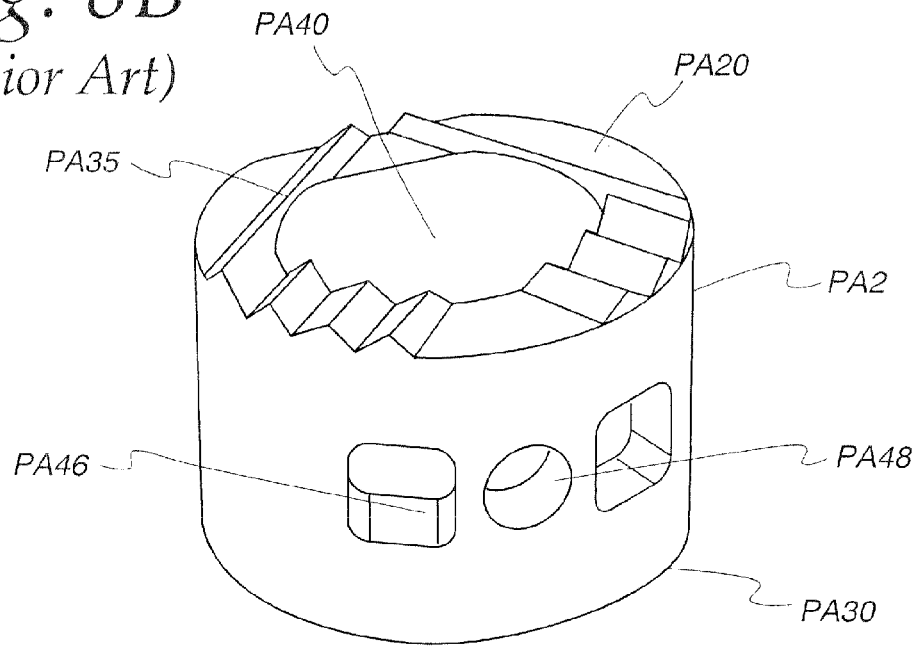
Figure 8G:
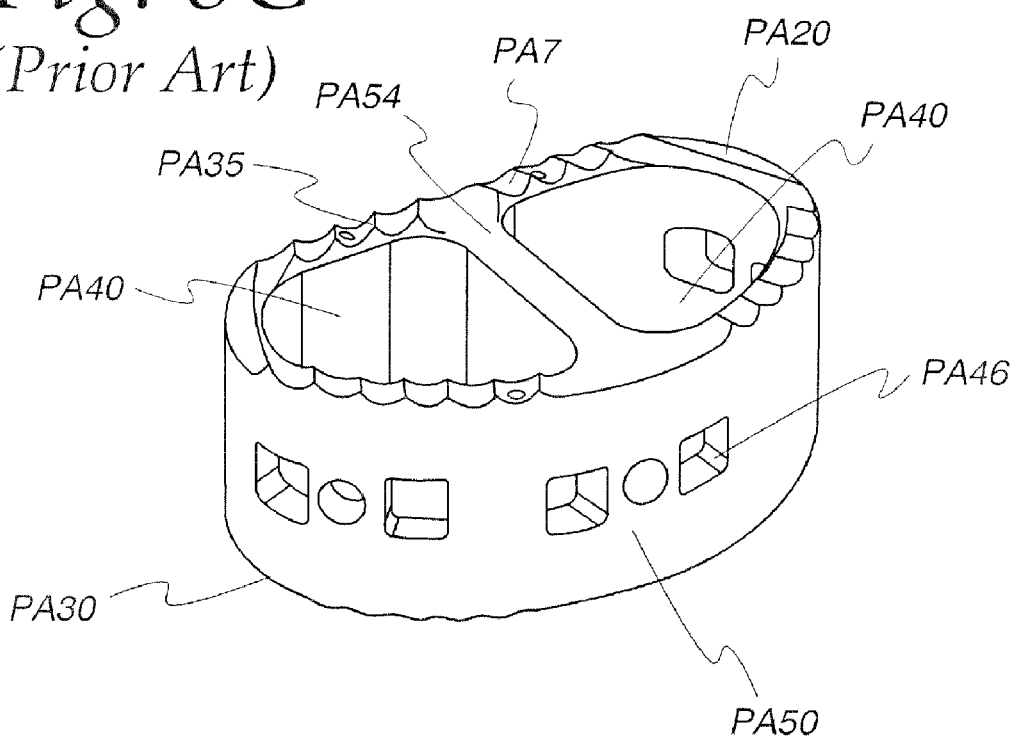
Figure 8H:
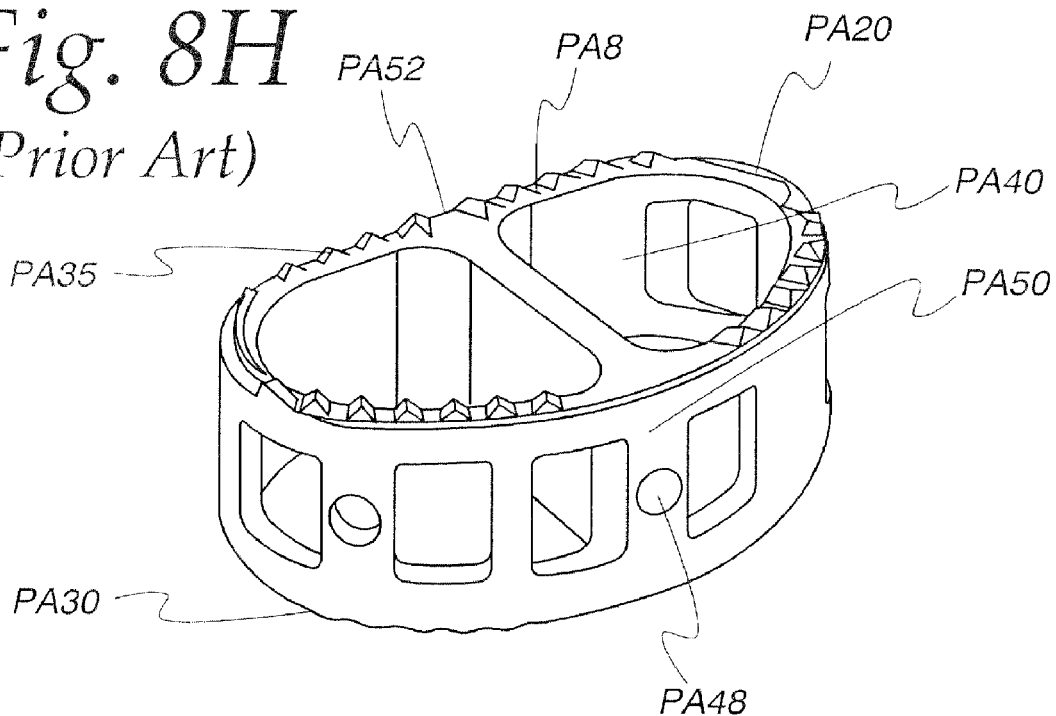
Figure 8I:
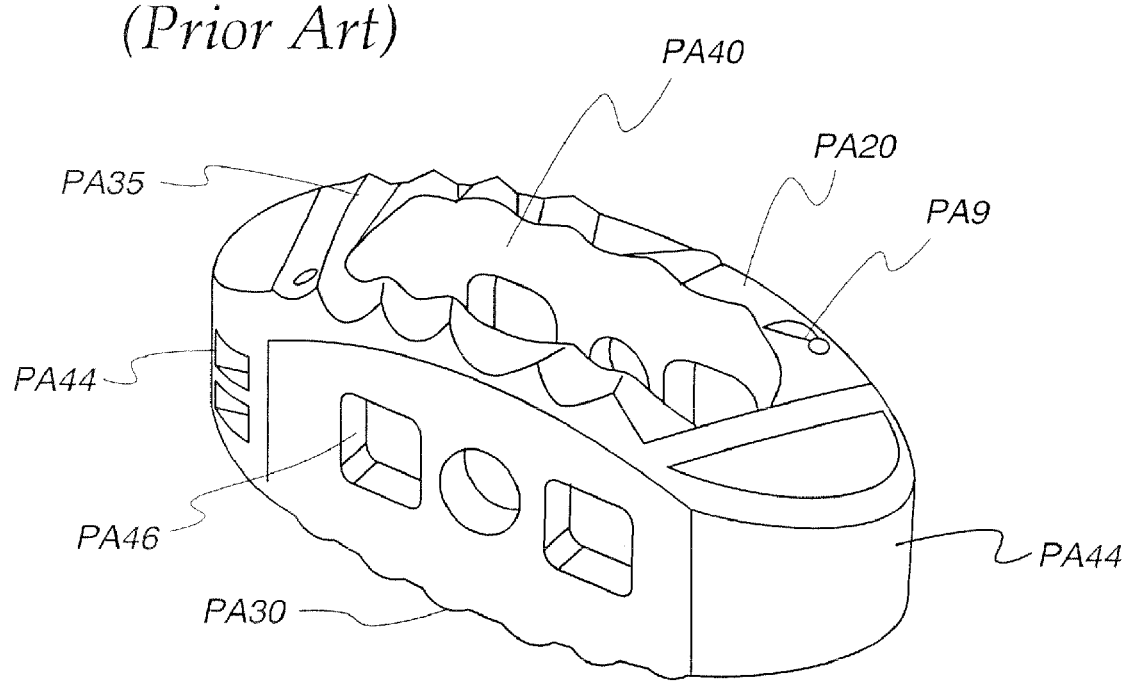
Figure 8J:
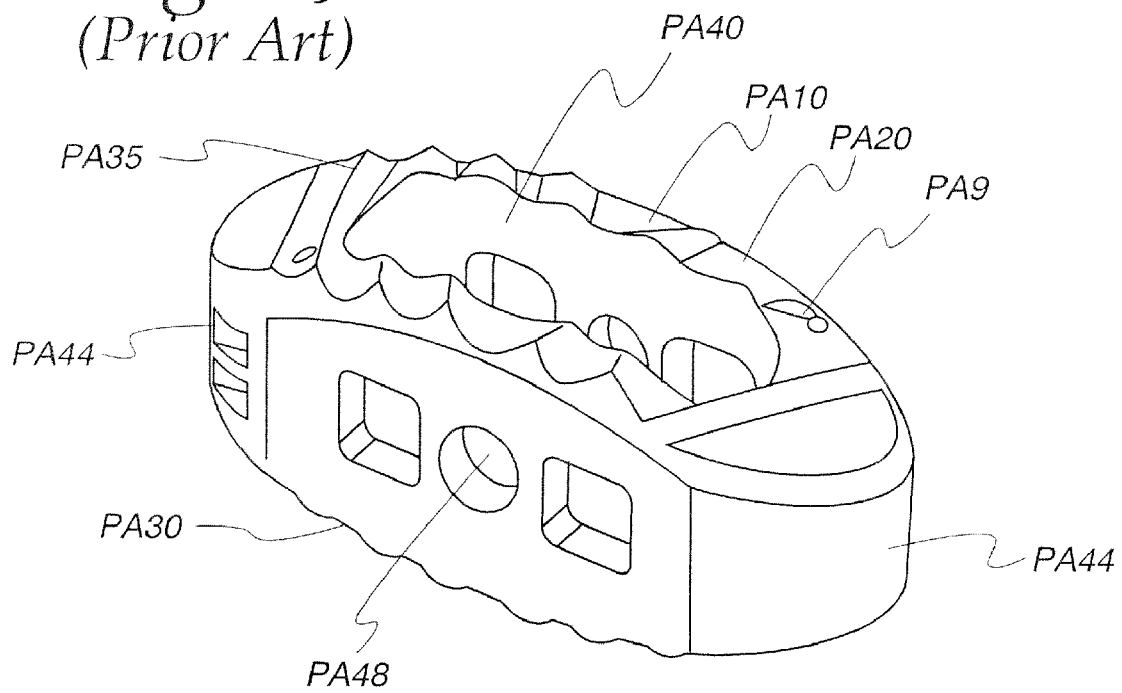
Figure 8K:
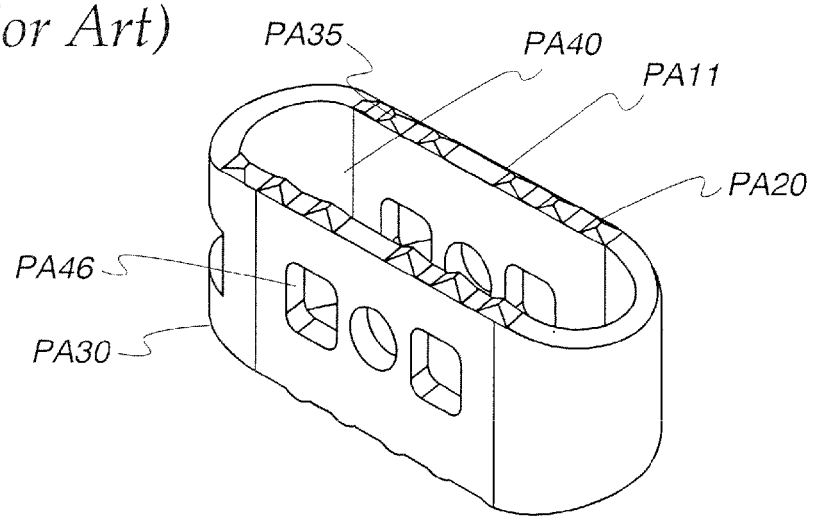
Figure 8L:
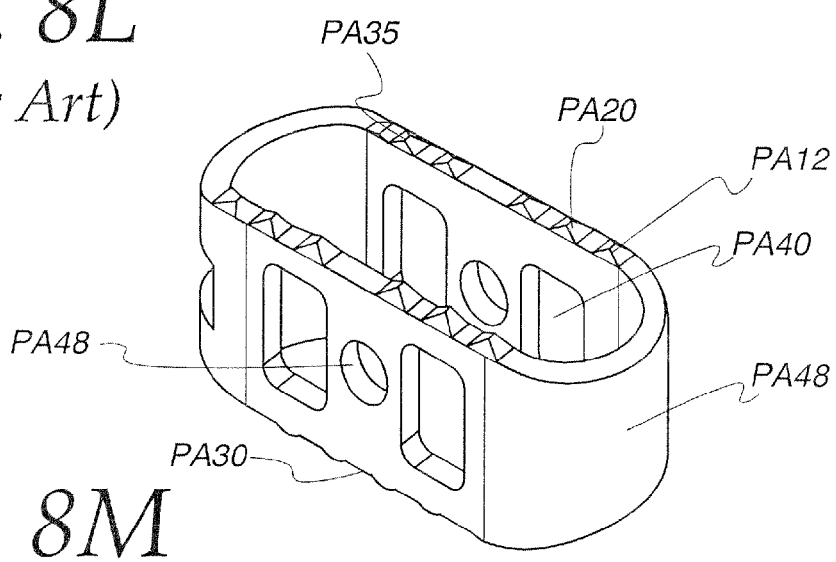
Figure 8M:
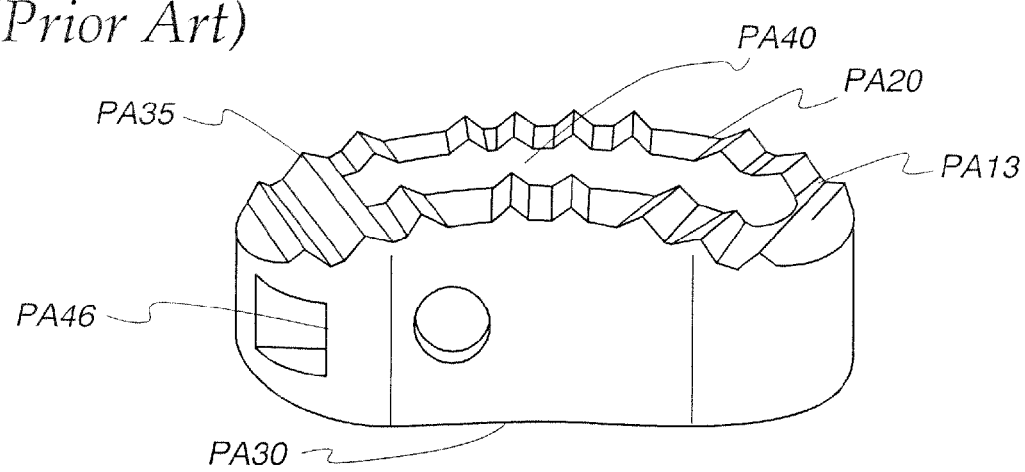

Embodiments of the invention can be incorporated in any number of interbody or vertebral body replacement devices, including for example, the devices shown in FIGS. 8A-8M. All of the interbody spacer devices shown in FIGS. 8A-8M are commercially available from Alphatec Spine™, Inc. (See website at: http://www.alphatecspine.com/products/interbody.asp). FIGS. 8A and 8B depict top perspective views of two configurations PA1, PA2 of the "Novel Cervical Interbody System" for use in an anterior cervical fusion procedure. FIGS. 8C-8F show top perspective views of four different configurations PA3, PA4, PA5, PA6 of the "Novel CP Vertebral Body Replacement System" for use in the thoracolumar spine (T1-15). FIGS. 8G and 8H illustrate two "Novel VC Spinal Spacers" PA7, PA8 for use in Anterior Lumbar Interbody Fusion (ALIF), made of PEEK or titanium. FIGS. 8I and 8J depict two "Novel SD" interbody spacer devices PA9, PA10 made of PEEK or titanium, for use in a Posterior Lumbar Interbody Fusion (PLIF). FIGS. 8K and 8L show two "Novel LCC Spacer" devices PA11, PA12 made of PEEK and titanium, for use in a Posterior Lumbar Interbody Fusion (PLIF). FIG. 8M illustrates a "Novel TL Spacer" device PA13 for use in a Transforaminal Lumbar Interbody Fusion (TLIF).

The spacer 100 is used in spinal fusion surgeries including ALIF, PLIF and TLIF procedures, wherein two or more vertebrae are joined or fused together for the treatment of spinal disorders such as spondylolisthesis, scoliosis, severe disc degeneration, or spinal fractures. The embodiments below are described primarily in the context of an ALIF procedure, though other spinal implants and procedures are also contemplated.

The spacer 100, shown schematically in FIG. 1 and contemplated to have the shapes of any of the conventional spacers PA1-PA13, described above, or any other suitable shape, includes first and second opposite surfaces 120 and 130 respectively configured to engage superiorly and inferiorly the end plates of adjacent vertebrae. As shown for the spacers in FIGS. 8A-8M, these corresponding surfaces PA20 and PA30 may have ridges, bumps or other protrusions PA35 to enhance engagement with the vertebral endplates. As shown in FIGS. 8A-8M, these surfaces PA20 may define openings PA40 (not shown in FIG. 1) to allow for fusion through the openings.

In the embodiment shown in FIG. 1, the first and second surfaces 120 and 130 are substantially flat and parallel. However, in other embodiments, the first and second surfaces can be angled relative to each other and may be non-flat, so as to better support adjacent vertebral bodies in a more natural spinal alignment configuration. For example, the first and second opposite surfaces, PA20 and PA30 of the interbody spacer shown in FIG. 8A, are slightly angled toward each other in the direction of the posterior surface PA42. Additionally, the first and second opposite surfaces, PA20 and PA30 of the interbody spacers shown in FIGS. 8I and 8J, are tapered toward each other toward the ends PA44 of the interbody spacers.

The spacer 100 has a proximal face 140 and a distal face 150, the proximal face 140 corresponding to the end that engages a delivery tool, such as with grooves or indentations PA46 or a threaded opening PA48 as shown in FIGS. 8A-8M. For an ALIF procedure, the proximal face 140 corresponds to the anterior face of the spacer (such as the convex surface PA50 in FIGS. 8G and 8H), and the distal face 150 corresponds to the posterior face of the spacer (such as the flat surface PA52 in FIG. 8H).

As illustrated in FIG. 1, the spacer 100 has three channels 155 for receiving suitable complementary stabilizers (discussed in further detail below), although it is to be understood that in other embodiments the spacer can have only one channel and in yet other embodiments, the space can have any number of channels.

The channels 155 interface with the first and second surfaces 120 and 130 of the spacer 100, as well as with at least the proximal surface 140 of the spacer 100. The channels 155 shown in FIG. 1 are shown extending through the body of the spacer 100, and interfacing with the distal surface 150 of the spacer 100. However, in other embodiments, the channels do not extend all the way through the spacer body to interface with the distal surface of the spacer and in other embodiments the channels 155 can interface with side surfaces 160 and 170. The channels 155 are preferably pre-cut into the spacer body 100 before insertion into the vertebral space during surgery. Where the spacer 100 has openings in the surfaces 120 and 130, the channels 155 may extend through solid portions of the spacer between the openings (such as through the intermediate bar PA54 shown in FIG. 8G, or may be interrupted by the openings PA40 so that the channels are provided on opposite sides of the openings PA40).

The interbody spacer 100 can be made of a rigid and durable biocompatible material such as titanium, titanium alloy, stainless steel iron steel and compositions thereof. Additionally, or alternatively, non-metal biocompatible materials such as cadaveric bone, polymers, elastomers, resins, ceramics and composites thereof can be employed. In a preferred embodiment, the interbody spacer is made of Polyetheretherketone (PEEK).

FIGS. 2 and 3 illustrate one embodiment of a stabilizer 200 suitable for use with the spacer 100 of FIG. 1, where FIG. 3 is an end view of the stabilizer of FIG. 2. The stabilizer 200 is configured to be partially received within the channels 155 of the spacer 100, with a portion extending out of the channel away from the surface 120 or 130 into the adjacent vertebral body. The stabilizer 200 is preferably thin enough to slice through bone, yet strong enough to hold onto the bone and stabilize the spacer 100 after insertion.

The stabilizer 200 as illustrated has three plates/walls 240, 250 and 260 attached together and configured in a "Z" shape as seen in FIG. 2. The stabilizer 200 can also be formed from a single plate which is bent to form the "Z" shape seen in FIG. 2. The stabilizer 200 is preferably made of titanium. However, it can also be made of any suitable material including, but not limited to: polycarbonate, urethane and PEEK. The stabilizer 200 preferably has sharp edges 264 and 266 which are thin and strong enough to slice through vertebral bone when a sufficient force is applied to the anterior surface 270 of the stabilizer 200. The stabilizer translates along a line (L in FIG. 2) under the applied force to be pressed into the bone portion to which it is aligned for this and other embodiments herein. The sharp edges 264, 266 may be at both ends so that the stabilizer can be inserted with either end thereof in a leading direction. The stabilizer 200 can also have self-retaining clips 272 attached to it to help keep the stabilizer attached to the spacer after insertion, as will be discussed in further detail below.

FIG. 4 shows the spacer 100 operably implanted within a spine 402 from the anterior side of the spine. The spine 402 includes bone portions/vertebrae 410, 420. The spine 402 also includes a diseased/damaged disk 430 that has been partially removed and replaced with the spacer 100.

During operation, the diseased/damaged disk 430 is partially or completely removed and preferably replaced with the spacer 100 with the proximal surface 140 of said spacer 100 facing anteriorly. Stabilizers 200 are then lined up with the channels 155 of the spacer 100 and driven by translational movement into the vertebral bodies 410, 420 by applying sufficient force to the stabilizers 200. The stabilizers 200 are simultaneously driven into the vertebral bones 410, 420 and received into their respective channels 155. However, it is to be understood that in some embodiments, stabilizers 200 can be inserted into the vertebral bone before spacer 100 is inserted.

As mentioned previously, the stabilizer 200 can further include self-retaining clips 272 (see FIG. 2) to fixedly attach the stabilizers 200 to the spacer 100 after insertion. The self-retaining clips 272 of FIG. 2 are attached to the stabilizer 200 and curve outward. The self-retaining clips 272 are made of a resilient material which allows them to retract during insertion. Once the stabilizers are inserted, the self-retaining clips 272 expand and push against the inner wall of the channel 155, resisting withdrawal. The inner walls of the channels 155 can be made rough or with notches to further aid the self-retaining clips 272 in resisting withdrawal.

It will be appreciated that the stabilizer 200 can have a variety of shapes and that the spacer 100 can be configured with complementary channels shaped to receive the stabilizer 200.

FIGS. 5A and 5B illustrate an alternative embodiment of a stabilizer 500 suitable for use with a spacer (not shown), having channels shaped to receive the stabilizer 500. FIG. 5A is a top perspective view of the stabilizer and FIG. 5B is an end view of the stabilizer of FIG. 5A. As illustrated, the stabilizer 500 has a substantially sinusoidal configuration. While not illustrated, the spacer for use with the stabilizer 500 has a complementary channel having a substantially sinusoidal shape configured to receive the stabilizer 500. The complementary channel can be oriented perpendicular to the upper and lower surfaces of the spacer, or in any other orientation which would allow the stabilizer 500 to fixedly attach the spacer to an adjacent vertebral body.

FIGS. 6A-6J show various end views of alternative embodiments of differently shaped stabilizers, by way of example and not limitation. One of skill in the art will appreciate that any number of differently shaped stabilizers can also be used, though not identically disclosed herein, without departing from the spirit of the invention. Many of these embodiments include a length configured to span between the spacer and the vertebral body, but also a transverse component (not shown in FIGS. 6A-6J) in both the spacer-engaging portion and the vertebral-body engaging portion configured to prevent separation between the spacer and vertebral body.

Figure 6A:
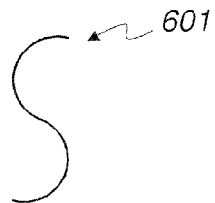
FIGS. 6A-6J depict end views of multiple embodiments of different stabilizers.

FIG. 6A illustrates an end view of a substantially "S" shaped stabilizer 601 suitable for use with a spacer (not shown), having channels shaped to receive the stabilizer 601. While not illustrated, the spacer for use with the stabilizer 601 has a complementary channel with a substantially "S" shape, configured to receive the stabilizer 601. The complementary channel can be oriented perpendicular to the upper and lower surfaces of the spacer, or in any other orientation which would allow the stabilizer 601 to fixedly attach the spacer to an adjacent vertebral body.

Figure 6B:
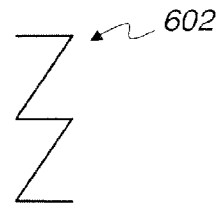
Figure 6C:
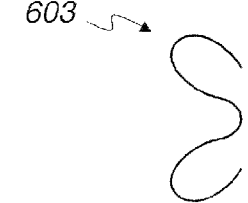
Figure 6D:
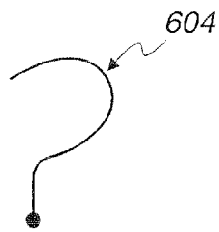
Figure 6E:
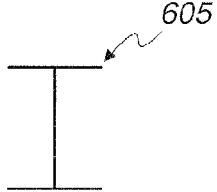
Figure 6F:
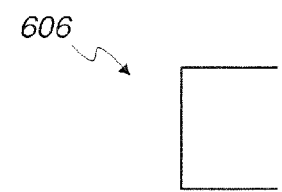
Figure 6G:
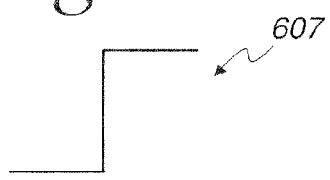
Figure 6H:
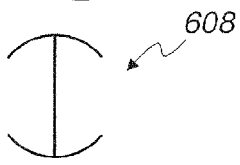
Figure 6I:
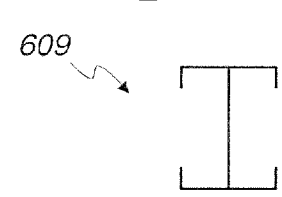

FIG. 6B illustrates an end view of a substantially double "Z" shaped stabilizer 602 configuration suitable for use with a spacer (not shown), having channels shaped to receive the stabilizer 602. While not illustrated, the spacer for use with the stabilizer 601 has a complementary channel having a substantially double "Z" shape, configured to receive the stabilizer 602. The complementary channel can be oriented perpendicular to the upper and lower surfaces of the spacer, or in any other orientation which would allow the stabilizer 602 to fixedly attach the spacer to an adjacent vertebral body.

FIGS. 6C-6J similarly illustrate end views of uniquely shaped stabilizers 603-610 configured for use with suitable spacers (not shown) having complementary channels shaped to receive each uniquely shaped stabilizer. The complementary channels can be oriented perpendicular to the upper and lower surfaces of the spacer, or in any other orientation which would allow the stabilizers to fixedly attach the spacers to an adjacent vertebral body.

Figure 7:
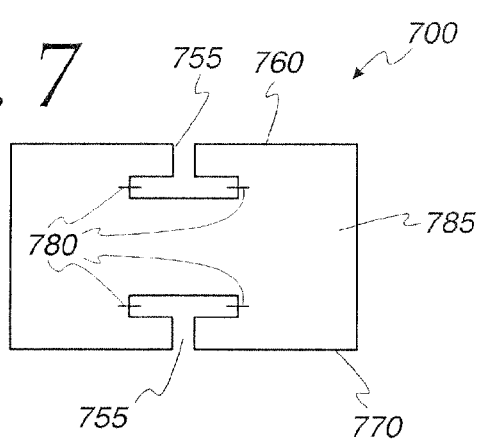
FIG. 7 is an end view of one embodiment of a spacer with self-retaining clips.

FIG. 7 depicts a front end view of yet another embodiment of an interbody spacer 700. The spacer 700 has channels 755 configured to receive at least one stabilizer, such as the stabilizer 605 (see FIG. 6E). The spacer 700 has first and second surfaces, 760 and 770 respectively, configured to engage adjacent vertebral end plates. In this embodiment, the first and second surfaces 760 and 770 are substantially parallel. However, in other embodiments, the first and second surfaces can be angled relative to each other, so as to better support adjacent vertebral bodies in a more natural spinal alignment configuration. The spacer 700 of the present embodiment has two channels 755 for receiving stabilizers such as the stabilizer 605, although it is to be understood that in other embodiments, the spacer 700 can have only one channel or more than two channels.

The interbody spacer 700 can be provided with self-retaining clips 780 to help keep the stabilizers attached to the spacer 700 after insertion. The self-retaining clips 780 can be attached to the proximal surface 785 of spacer 700 and partially extend in front of the channels 755. Preferably, the self-retaining clips 780 have a first and a second position. In the first position, the clip 780 is retracted during insertion of the stabilizer. After the stabilizer is inserted, the clip 780 extends, assuming a second position. The self-retaining clips 780 can be made of a resilient material which allows them to bend inward during insertion of a stabilizer. Once the stabilizer is inserted into the spacer, the self-retaining clips 780 can "pop out" towards their original positions to impede withdrawal of the stabilizers.

Figure 9:
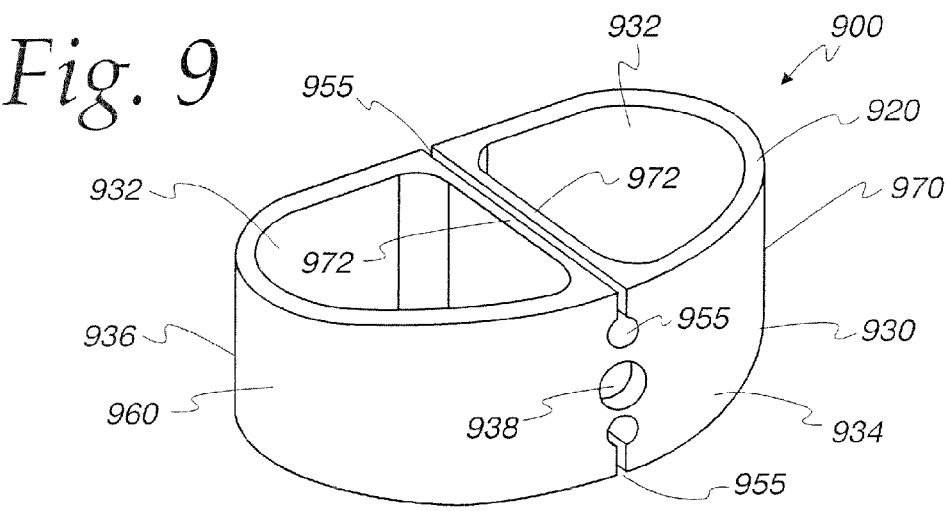
FIG. 9 is a schematic, perspective view of another embodiment of an interbody spacer showing a superior surface and an anterior surface thereof.

FIG. 9 illustrates schematically another embodiment of an interbody spacer 900, similar to the spacers seen in FIGS. 8G and 8H depicting various "Novel VC Spinal Spacers" for use in Anterior Lumbar Interbody Fusion (ALIF), which are commercially available from Alphatec Spine™, Inc. (See website at: http://www.alphatecspine.com/products/interbodv.asp).

In preferred embodiments, the spacer 900 is used in spinal fusion surgeries, including ALIF procedures, though other implants and procedures are also contemplated.

The spacer 900, shown schematically in FIG. 9, includes first and second opposite surfaces, 920 and 930 respectively configured to engage superiorly and inferiorly the end plates of adjacent vertebrae. These surfaces 920 and 930 may have ridges, bumps or other protrusions to enhance engagement with the vertebral endplates as discussed above, and shown in FIGS. 8A-8M. As shown in FIG. 9, the first and second opposite surfaces, 920 and 930 may define openings 932 to allow for fusion through the openings. In the embodiment shown in FIG. 9, the first and second surfaces 920 and 930 are substantially parallel. However, in other embodiments, the first and second surfaces can be angled relative to each other, so as to better support adjacent vertebral bodies in a more natural spinal alignment configuration, as discussed previously.

The spacer 900 has a proximal face 934 and a distal face 936, the proximal face 934 corresponding to the end that engages a delivery tool, such as with grooves, indentations or a threaded opening 938, similar to that discussed above with reference to FIGS. 8A-8M. For an ALIF procedure, the proximal face 934 corresponds to the anterior face of the spacer and the distal face 936 corresponds to the posterior face of the spacer.

As illustrated in FIG. 9, the spacer 900 has two channels 955 for receiving suitable stabilizers (discussed in further detail below), although it is to be understood that in other embodiments the spacer can have only one channel and in yet other embodiments, the spacer can have any number of channels.

The channels 955 interface with the first and second surfaces 920 and 930 of the spacer 900, as well as with at least the proximal surface 934 of the spacer 900. The channels 955 shown in FIG. 9 extend through the body of the spacer 900, and interface with the distal surface 936 of the spacer 900. However, in other embodiments, the channels do not extend all the way through the spacer body to interface with the distal surface of the spacer and in other embodiments the channels 950 can interface with side surfaces 960 and 970. The channels 955 are preferably pre-cut into the spacer 900 before insertion into the vertebral space during surgery. Where the spacer 900 has openings 932 in the surfaces 920 and 930, the channels 955 may extend through solid portions of the spacer 900 between the openings 940 (such as through the intermediate bar 972 shown in FIG. 9), or they may be interrupted by the openings 932 so that the channels 955 are provided on opposite sides of the openings 932.

Figure 10:
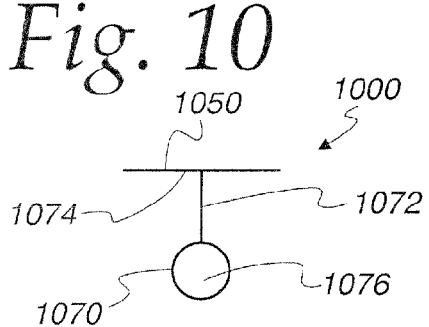
FIG. 10 is an end view of yet another embodiment of a stabilizer.
Figure 11:
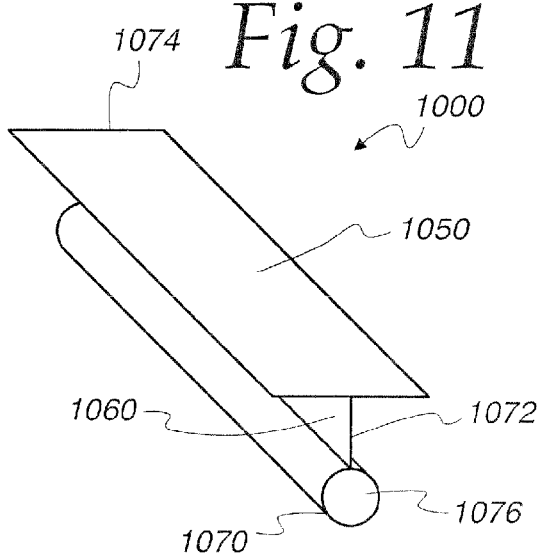
FIG. 11 is a perspective view of the stabilizer of FIG. 10.

FIGS. 10 and 11 illustrate one embodiment of a stabilizer 1000 suitable for use with the spacer 900 of FIG. 9, where FIG. 10 is an end view of the stabilizer 1000 and FIG. 11 is a perspective view of the stabilizer 1000. The stabilizer 1000 is configured to be partially received within the channels 955 of the spacer 900, with a portion extending out of the channel 955 away from the surface 920 or 930 into the adjacent vertebral body. The stabilizer 1000 is preferably thin enough to slice through bone, yet strong enough to hold onto the bone and stabilize the spacer 900 after insertion. The stabilizer 1000, as illustrated, has two plates/walls 1050 and 1060 and a cylindrically-shaped wall/retaining member 1070 fixedly attached together with the walls 1050, 1060 configured in a "T" shape as seen in FIG. 10. The stabilizer 1000 is preferably made of metal but it can also be made of any suitable material including, but not limited to: Ti-6AI-4V, ELI, ASTM F 136, commercially pure titanium (for example, Ti-CP2, ASTM F 67, CPTi, etc.). The plates 1050 and 1060 of stabilizer 1000 preferably have sharp edges 1072 and 1074 which are thin and strong enough to slice through vertebral bone when a sufficient force is applied to the anterior surface 1076 of stabilizer 1000. Stabilizer 1000 can also have self-retaining clips (not shown) attached to it to help keep the stabilizer 1000 attached to the spacer 900 after insertion, as discussed previously.

Figure 12:
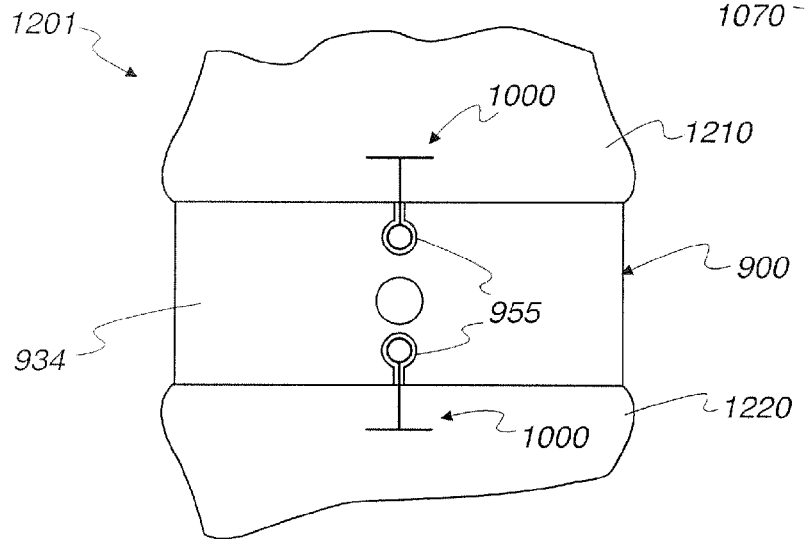
FIG. 12 is an end view of the spacer of FIG. 9 with the two stabilizers according to FIG. 10 inserted into the spacer.

FIG. 12 is an end view of the spacer 900 of FIG. 9 operably implanted within a spine 1201 from the anterior side of the spine. The spacer 900 is inserted between two bone portions/vertebrae 1210 and 1220 and two stabilizers 1000, according to FIGS. 10 and 11, are inserted into the channels 955 of the spacer 900 and into the adjacent vertebral bodies 1210 and 1220.

During operation, the diseased/damaged disk (not shown) is partially or completely removed and preferably replaced with a spacer 900 with the proximal surface 934 of said spacer 900 facing anteriorly. Stabilizers 1000 are then lined up with the channels 955 of the spacer 900 and driven translationally along a line into vertebral bodies 1210 and 1220 by applying sufficient force to the stabilizers 1000. The stabilizers 1000 are simultaneously driven into the vertebral bones 1210 and 1220 and received into their respective channels 955. However, it is to be understood that in some embodiments, stabilizers 1000 can be inserted into the vertebral bones 1210 and 1220 before spacer 900 is inserted. It is further conceivable, with this and other embodiments, that the stabilizers could be pre-joined to their respective spacer before the stabilizer is translated into the bone portions.

It should be understood that all of the particular structures described in each embodiment may be used in any other embodiment. That is, the invention contemplates that the different features in the embodiments disclosed herein may be interchanged.

Figure 13:
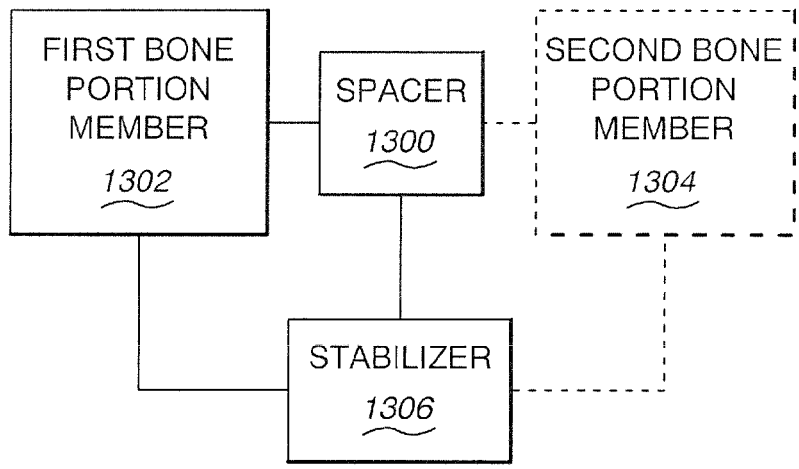
FIG. 13 is a schematic representation of an inventive system, including at least one bone portion/member with an interbody spacer fixed thereagainst utilizing a stabilizer.

As noted previously, it is contemplated that the invention can be practiced as part of any medical procedure involving the placement of a spacer between adjacent bone portions. This generic concept is shown schematically in FIG. 13, wherein a spacer 1300, representing all spacer configurations disclosed herein, as well as others, is operatively joined to at least a first bone portion 1302. It is conceivable that the spacer 1300 would be joined to only the first bone portion 1302. However, more commonly, the invention would be practiced by using the spacer 1300 between the first bone portion 1302 and a second bone portion 1304, which is shown to be optional by the depiction of the latter schematically in FIG. 13 in dotted lines. The stabilizer 1306, as shown in FIG. 13, is intended to represent all stabilizer constructions disclosed herein, as well as others. The stabilizer 1306 operatively interacts between the spacer 1300 and either of the bone portions 1302, 1304.

With the system as shown in FIG. 13, the spacer 1300 is configured to be placed between the first and second bone portions 1302, 1304. The stabilizer 1306 is configured to be joined: a) to each of the first bone portion 1302 and spacer 1300; and b) to at least one of the first bone portion 1302 and spacer 1300 by being translated relative to the at least one of the first bone portion 1302 and spacer 1300 along a first line.

As noted previously, the stabilizer 1306 preferably extends into its associated bone portion 1302, 1304 over a majority of the dimension of that bone portion 1302, 1304 along a corresponding first translation line L, as seen in FIG. 2 for the stabilizer 200.

As seen in FIGS. 2 and 3, the stabilizer 200 has the aforementioned plates/walls 240, 250, 260, with a first and second of the walls 250, 260 having facing surfaces S1, S2, respectively. With the stabilizer operatively positioned, as seen in FIG. 4, a part P1 of the vertebra 420 and a part P2 of the spacer 100 are captive between the facing surfaces S1, S2 to stabilize the spacer and bone portion/member 420.

Because each of the plates/walls 240, 250, 260 has a substantial width dimension transversely to the line L, the connection is stabilized in all critical dimensions. Preferably, the plates/walls 240, 260 extend into the spacer 100 along a majority of the dimension of the spacer 100 along the line L. More preferably, the spacer walls 240, 250, 260 extend along substantially the entire dimension of the spacer 100 along the line L.

Each of the stabilizer configurations defined herein has surfaces that produce the above captive arrangement through which the parts P1, P2 are confined against movement away from each other in a direction transversely to the line L. By reason of the depicted configurations, these stabilizers also produce multidimensional reinforcement between the fused components.

As seen in FIG. 4, the spacer surface 120 abuts to an adjacent surface AS1 on the vertebra 410, with the opposite spacer surface 130 abutting the adjacent surface AS2 on the vertebra 420. It is contemplated that the stabilizers 200 extend through at least one of the surfaces 120, AS1 and 130, AS2 at locations where the surfaces abut. More preferably, each stabilizer extends continuously through each of the adjacent faces 120, AS1 and 130, AS2.

It is conceivable that a spacer could be devised having a U-shaped configuration, with spaced legs parallel to each other and the line L, such that the spacer does not penetrate any of the surfaces 120, 130, AS1, AS2. This spacer would be inserted similarly in a translational path.

As seen in FIG. 4, the surfaces 120, 130, AS1, AS2 are shown to be generally flat and parallel to each other. The translation line for the stabilizers 200 during assembly is substantially parallel to each of the surfaces 120, 130, AS1, AS2.

As also seen in FIG. 4, the inventive stabilizer 200 is constructed so that it extends only partially through the dimension of the spacer 100 between the surfaces 120, 130.

As further seen in FIG. 4, each of the components 410, 420, 100 has a peripheral surface, PS1, PS2, PS3. The stabilizers 200 can be constructed so that the stabilizers do not project from any of the exposed peripheral surfaces PS1, PS2, PS3. While preferred, this is not a requirement.

Additional variations of the inventive structure are shown in FIGS. 14-21.

Figure 6J:
Figure 14:
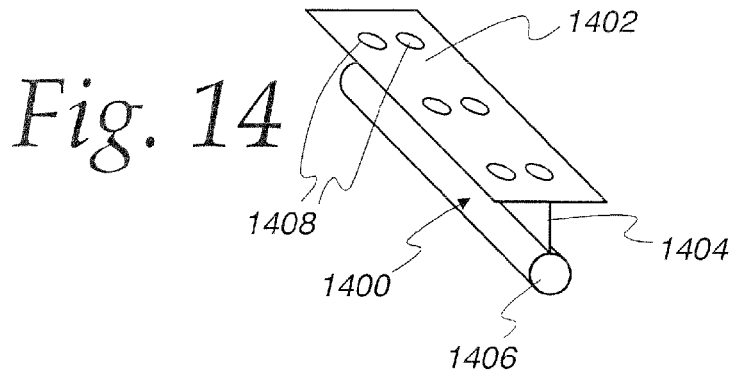
FIG. 14 is a perspective view of a modified form of stabilizer, according to the invention.

In FIG. 14, a fenestrated form of stabilizer 1400 is depicted with a configuration corresponding to the stabilizer 610 in FIG. 6J. The stabilizer 1400 has flat walls 1402, 1404 which combine to produce a "T" shape. A cylindrical wall 1406 is provided at the bottom of the "T".

The wall 1402, that is embedded in the bone, has discrete openings 1408 into which bone can grow to thereby further secure the connection between the stabilizer 1400 and bone.

Figure 15:
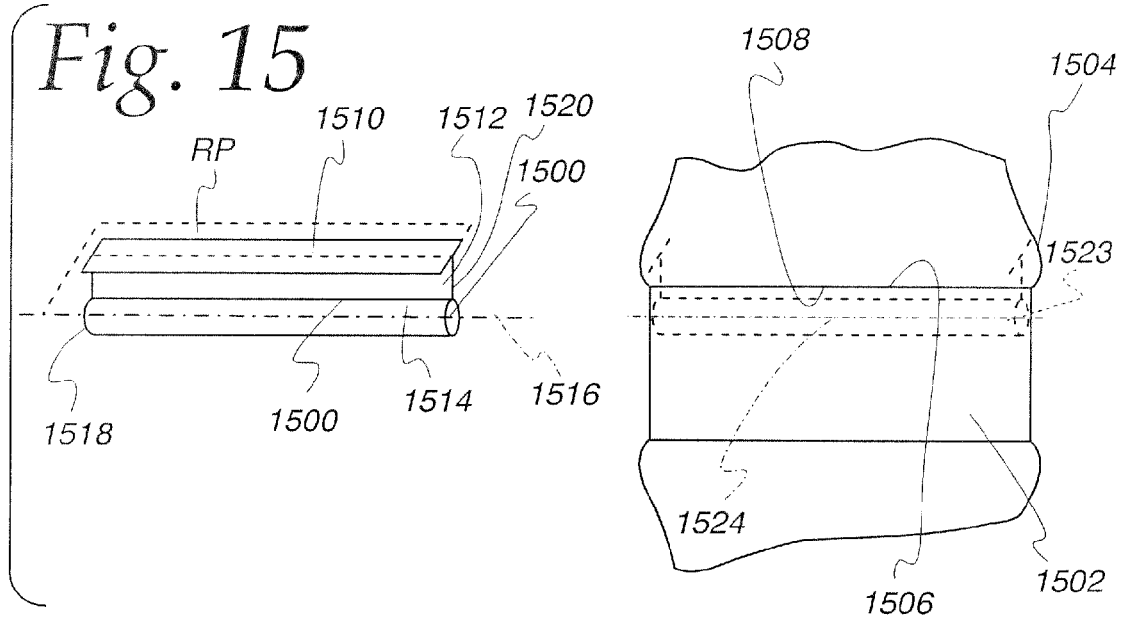
FIG. 15 is a fragmentary, perspective view showing a spacer against a bone portion and a further modified form of stabilizer that is configured to urge the bone portion and spacer towards each other as the stabilizer is inserted.

In FIG. 15, a stabilizer 1500 is shown for use in conjunction with a spacer 1502 and bone portion 1504 to cause facing surfaces 1506, 1508 on the spacer 1502 and bone portion 1504 to be urged towards each other with a progressive camming action as the stabilizer 1500 is inserted.

The stabilizer 1500 has flat walls 1510, 1512 that produce a "T" shape, at the bottom of which a cylindrical wall 1514 is provided. The wall 1510 resides within a reference plane RP. The wall 1514 has a central axis 1516 that is non-parallel to the reference plane RP. More specifically, the axis 1516 is oriented so that the space between the reference plane RP and axis 1516 increases between the trailing end 1518 and leading end 1520.

The spacer 1502 has a channel 1523 to accept the wall 1514 and a part of the wall 1512. The axis 1524 of the channel portion that accepts the cylindrical wall 1514 is substantially parallel to the spacer surface 1506. As a result, as the leading end 1520 is translated into the channel 1523 and the wall 1510 cuts into the bone portion 1504, the movement of the cylindrical wall 1514 into the channel 1523 produces a camming action that progressively urges the surfaces 1506, 1508 against each other.

In FIG. 16, a stabilizer 1600 is shown in relationship to a spacer 1602 and bone portion 1604, wherein a similar camming action is produced by essentially reversing the construction shown in FIG. 15. That is, the axis 1606 on the spacer 1602, that corresponds to the axis 1524, is inclined relative to the spacer surface 1608, whereas the axis 1610 for the cylindrical wall 1612 is substantially parallel to a reference plane RP1 containing the flat wall 1616.

Using the concepts disclosed in FIGS. 15 and 16, the components can be configured to produce the desired compressive force between a spacer and bone portion, as well as potentially producing such a force at both sides of the bone portion.

While the walls 1514, 1612 are shown with a cylindrical shape, it is contemplated that the shape may be non-circular in cross-section so as to be keyed within the cooperating channel to further stabilize the connected spacer and bone portion.

The invention also contemplates that locking assemblies might be incorporated into the stabilizers and spacers to avoid inadvertent backing out or extension of the particular stabilizer at a fusion location. In FIG. 17, one form of locking assembly is shown at 1700. A stabilizer 1702 has the same general construction as the stabilizer 1600 in FIG. 16, with the exception that there is an enlargement 1704 on the trailing end thereof. A cooperating spacer 1706 has a complementary channel 1708 including an enlarged receptacle 1710 that is complementary to the enlargement 1704. The enlargement 1704 and receptacle 1710 define cooperating connecting parts on the locking assembly 1700. With the stabilizer 1702 translated along the line L to a fully inserted position, the enlargement 1704 snap fits into the receptacle 1710 to produce a detent-type action.

In the depicted embodiment, the enlargement 1704 is countersunk so as to not project from the spacer 1706. However, the parts could be configured so that there is a flush relationship or a projection of the enlargement 1704 from the spacer 1706.

With this arrangement, the locking assembly 1700 maintains the stabilizer 1702 in its operative position shown in FIG. 17.

Another type of locking assembly is shown in two different forms in FIGS. 18-20. The locking assembly in FIGS. 19 and 20 consists of a reconfigurable body 1800 on a stabilizer 1802. The stabilizer 1802 is directed into a channel 1806 on a spacer 1808. The channel 1806 has a flared region 1810 inset from a wall portion 1812. The flared region 1810 defines an enlarged receptacle bounded by an annular shoulder/surface 1814 set inwardly from a surface 1815 on the spacer 1808.

With the stabilizer 1802 translated into the channel 1806, a bifurcated end 1820 of a cylindrical wall 1822 resides at the flared region 1810. The bifurcation at the end 1820 produces diametrically opposite tabs 1830, 1832 between which a threaded spreader element 1840 can be directed. The spreader element 1840 has an outer surface 1842 with a portion having a progressively increasing diameter. By threading the spreader element 1840 into the wall 1822, the tabs 1830, 1832 are reconfigured by bending radially outwardly to move into the receptacle defined by the flared region and cause surfaces on the tabs 1830, 1832 to seat behind the annular shoulder/ surface 1814, whereupon the stabilizer 1802 is blocked by the surface 1814 that faces oppositely to and confronts the surfaces of the tabs 1830, 1832 from being withdrawn. The spreader element 1840 thus changes the locking assembly from the assembly state, as shown in solid lines in FIGS. 19 and 20, to a locked state as shown in dotted lines in FIG. 20. The tabs 1830, 1832 and flared region 1810 make up cooperating connecting parts on the locking assembly.

In FIG. 18, the locking assembly consists of corresponding tabs 1830', 1832', on a stabilizer 1802', that cooperate with a complementarily-shaped the region 1810' of a channel 1806'. The tabs 1830', 1832' may spring oppositely into the region 1810' without requiring insertion of a separate spreader element.

As an alternative form of locking assembly, as shown in FIG. 21, a stabilizer 1900 is provided with a locking tab 1902. The locking tab 1902 has a bore 1904 therethrough and is bent on site or pre-bent to be substantially orthogonal to the plane of a wall 1906 on the stabilizer 1900. With this arrangement, the locking tab 1902 overlies a part of the exposed bone portion 1910 whereby a threaded fastener 1920 can be directed therethrough. The fastener 1920 is preferably a threaded component. A similar tab (not shown) might be provided to be securable to the cooperating spacer 1930 in like fashion.

Threads 1940 might be provided around the bore 1904. The threads 1940 may be interrupted or placed at multiple points to allow for a controlled cross-threading of the head 1942 of the fastener 1920 as it is inserted. This allows the fastener 1920 to be inserted at any optimal angle.

In other variations, stabilizers, such as the stabilizer 1400, may be treated by applying bone ingrowth coating, as on the wall 1402. The coating may be in the form of beads, mesh, or hydroxyappetide. This promotes rapid ingrowth into the openings 1408. This same concept may be used on all other stabilizers described herein.

Each of the described embodiments might be further modified by additionally using screws, adhesives, or other supplementary fixation structure.

The foregoing disclosure of specific embodiments is intended to be illustrative of the broad concepts comprehended by the invention.

The invention claimed is:

1. An apparatus for stabilizing first and second adjacent bone portions, the apparatus comprising:
 a spacer configured to be placed between the first and second bone portions; and
 at least one stabilizer configured to be joined: a) to each of the first bone portion and the spacer; and b) to at least one of the first bone portion and spacer by being translated along a first line relative to the at least one of the first bone portion and spacer,
 the at least one stabilizer comprising first and second walls that are fixedly connected to each other and respectively define first and second surfaces that face each other,
 whereby a part of each of the spacer and first bone portion can be located captively between the first and second surfaces so that the parts of the spacer and first bone are confined by the first and second surfaces against movement away from each other and transversely to the first line by the first and second surfaces with the stabilizer joined to each of the spacer and first bone portion.

2. The apparatus according to claim 1 wherein the spacer has a pre-formed channel to receive the at least one stabilizer.

3. The apparatus according to claim 1 wherein each of the facing first and second surfaces has a substantial dimension transverse to the first line.

4. The apparatus according to claim 1 wherein the spacer has a first dimension extending along the first line and the first and second walls extend into the spacer over a majority of the first dimension.

5. The apparatus according to claim 1 wherein the first bone portion and spacer have adjacent facing surfaces and the at least one stabilizer is configured to extend through each of the adjacent facing surfaces.

6. The apparatus according to claim 1 wherein the facing first and second surfaces are configured to progressively urge the first bone portion and spacer against each other as the at least one stabilizer is translated relative to the at least one of the first bone portion and spacer.

7. The apparatus according to claim 1 wherein the at least one stabilizer is translatable relative to the spacer into an operative position and there is a locking assembly on the at least one stabilizer and spacer that maintains the at least one stabilizer in the operative position with the spacer between the first and second bone portions.

8. The apparatus according to claim 7 wherein the locking assembly comprises cooperating snap fit connecting parts, one each on the spacer and at least one stabilizer.

9. The apparatus according to claim 8 wherein the connecting parts comprise oppositely facing surfaces on the spacer and at least one stabilizer that confront each other.

10. The apparatus according to claim 7 wherein the locking assembly is reconfigurable between an assembly state and a locked state.

11. The apparatus according to claim 10 wherein the locking assembly comprises a reconfigurable wall and a spreader element that is directed into the reconfigurable wall to thereby change the locking assembly from the assembly state into the locked state.

12. The apparatus according to claim 7 wherein the locking assembly comprises at least one locking tab on the at least one stabilizer that overlies at least one of the first bone portion and spacer and is secured to the at least one of the first bone portion and spacer.

13. The apparatus according to claim 1 wherein one of the first and second walls comprises a cylindrical member with a central axis that is substantially parallel to the first line.

14. The apparatus according to claim 13 wherein the other of the first and second walls has a flat shape.

15. The apparatus according to claim 14 wherein another wall connects between the first and second walls and has a flat shape that defines in conjunction with the other of the first and second walls a "T" shape.

16. A method for stabilizing first and second adjacent bone portions, the method comprising the steps of:
 providing a spacer;
 placing the spacer between the first and second adjacent bone portions;
 providing a stabilizer with fixedly connected first and second walls that are spaced from each other and respectively define first and second surfaces that face each other;
 joining the stabilizer to the spacer; and
 joining the stabilizer to the first bone portion by translating the stabilizer relative to the first bone portion along a first line,
 a part of each of the spacer and first bone portion residing captively between the first and second surfaces so that the parts of the spacer and first bone portion are confined against movement away from each other and transversely to the first line by the first and second surfaces with the stabilizer joined to each of the spacer and first bone portions.

17. The method according to claim 16 wherein the spacer comprises first and second oppositely facing surfaces each facing one of the first and second bone portions and the step of translating the stabilizer comprises translating the stabilizer relative to the first bone portion along a first line that is substantially parallel to at least one of the oppositely facing surfaces.

18. The method according to claim 17 wherein the first bone portion has a surface that faces the first surface on the spacer and the step of translating the stabilizer comprises translating the stabilizer so that the stabilizer extends through each of the surface on the first bone portion and the first spacer surface.

19. The method according to claim 16 wherein one of the first and second walls has a cylindrical shape.

20. The method according to claim 19 wherein the other of the first and second walls has a flat shape.

21. The method according to claim 19 wherein another wall connects between the first and second walls and has a flat shape that defines in conjunction with the other of the first and second walls a 'T' shape.

22. The method according to claim 21 wherein the stabilizer has a length and the first, second and another walls each extends continuously over substantially the entire length of the stabilizer.

23. The method according to claim 21 wherein the other and the another of the walls have sharp edges that slice through the first bone portion as the stabilizer is translated relative to the first bone portion.

24. The method according to claim 16 further comprising the step of providing cooperating connecting parts on the stabilizer and spacer that snap fit together as the stabilizer is translated relative to the spacer.

25. The method according to claim 16 further comprising the step of providing oppositely facing surfaces on the spacer and stabilizer that face generally along the first line and causing the oppositely facing surfaces to confront each other with the stabilizer joined to the spacer to block relative movement between the stabilizer and spacer along the first line.

* * * * *